United States Patent
Yamatani

(10) Patent No.: US 8,038,610 B2
(45) Date of Patent: Oct. 18, 2011

(54) MEDICAL INSTRUMENT INTRODUCTION DEVICE AND METHOD OF INTRODUCING MEDICAL DEVICE

(75) Inventor: Ken Yamatani, Tokyo (JP)

(73) Assignee: Olympus Medical Systems Corp. (JP)

(*) Notice: Subject to any disclaimer, the term of this patent is extended or adjusted under 35 U.S.C. 154(b) by 263 days.

(21) Appl. No.: 12/121,869

(22) Filed: May 16, 2008

(65) Prior Publication Data

US 2009/0287240 A1 Nov. 19, 2009

(51) Int. Cl.
*A61B 1/313* (2006.01)
(52) U.S. Cl. ........................................ 600/184
(58) Field of Classification Search .............. 600/184; 606/108, 192; 604/174
See application file for complete search history.

(56) References Cited

U.S. PATENT DOCUMENTS

| | | | |
|---|---|---|---|
| 5,338,302 A | | 8/1994 | Hasson |
| 5,833,664 A | * | 11/1998 | Seare, Jr. .................. 604/174 |
| 5,935,107 A | * | 8/1999 | Taylor et al. ............ 604/164.04 |
| 2004/0111061 A1 | * | 6/2004 | Curran ...................... 604/174 |
| 2004/0116868 A1 | * | 6/2004 | Forman et al. ............ 604/174 |
| 2007/0167680 A1 | | 7/2007 | Miyamoto et al. .......... 600/106 |

FOREIGN PATENT DOCUMENTS

| | | |
|---|---|---|
| WO | WO 02/04064 | 1/2002 |
| WO | WO 02/07618 | 1/2002 |

OTHER PUBLICATIONS

Extended European Search Report dated Sep. 10, 2009 in corresponding European Patent Application No. EP 09 00 6595 (English language).

* cited by examiner

*Primary Examiner* — Ryan Severson
(74) *Attorney, Agent, or Firm* — Ostrolenk Faber LLP

(57) ABSTRACT

A medical instrument introduction device for introducing a medical instrument into a living body provided with; a rigid main body provided with a lumen, a first fixing portion disposed on the main body to fix the main body on the first septate of the living body, and a second fixing portion disposed on a distal end side of the main body with respect to the first fixing portion and to fix the main body on a second septate which is different from the first septate.

4 Claims, 11 Drawing Sheets

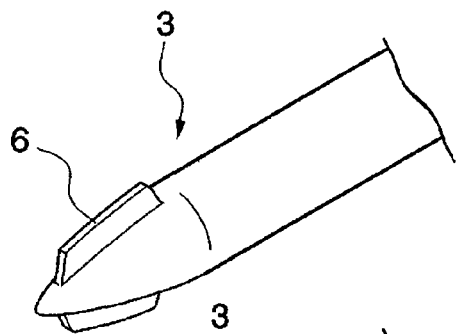
FIG. 5A
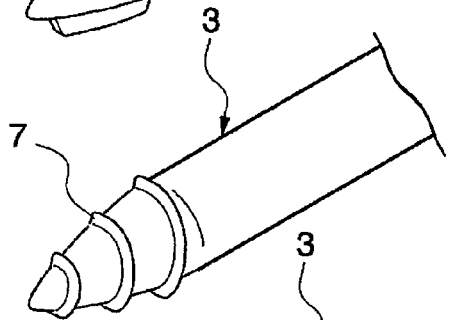
FIG. 5B
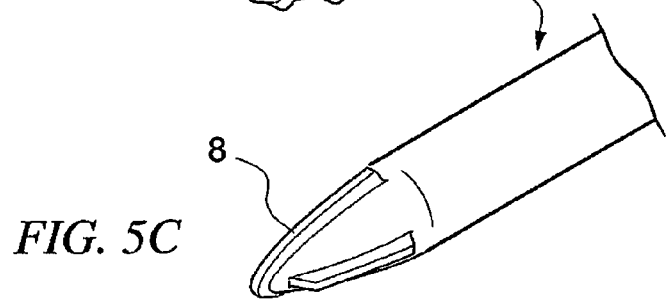
FIG. 5C
FIG. 6
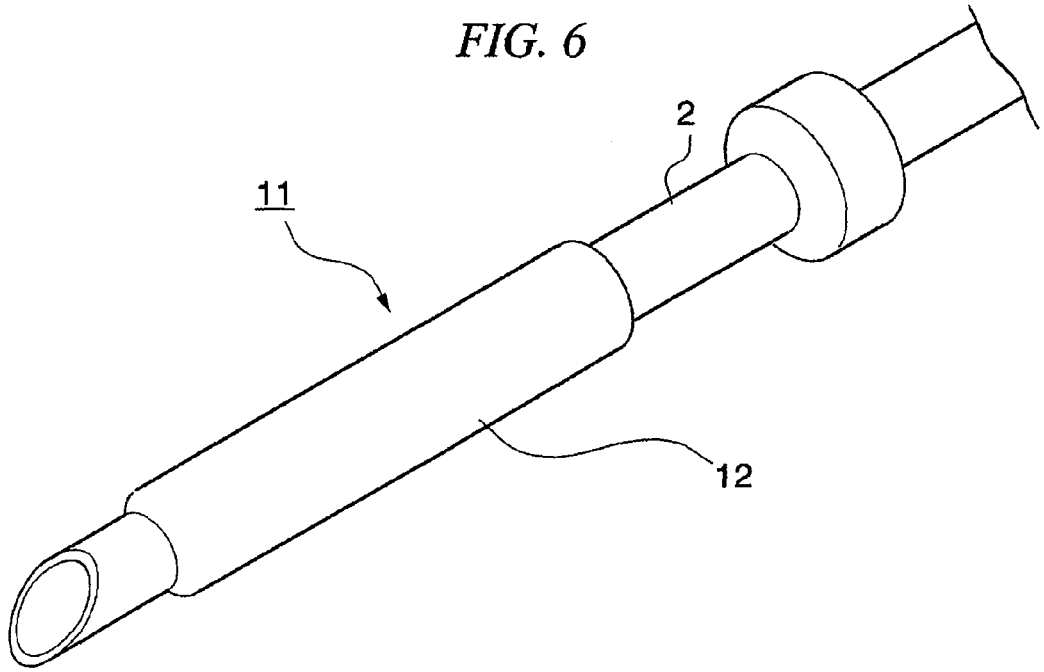

MEDICAL INSTRUMENT INTRODUCTION DEVICE AND METHOD OF INTRODUCING MEDICAL DEVICE

BACKGROUND OF THE INVENTION

1. Field of the Invention

The present invention relates to a medical instrument introduction device employed when a medical instrument is inserted into a body cavity and a method of introducing the medical instrument.

2. Description of Related Art

Cholecystectomy and other various procedures using laparoscopy and the like are examples of minimally invasive therapies which have been carried out conventionally. In this type of laparoscopic procedure, a plurality of openings are made in the abdominal wall and various instruments are inserted through these openings.

In recent years, designs have been proposed to carry out these procedures by inserting a flexible endoscope into the patient via a natural orifice, e.g., mouth, naris, anus, etc., with the goal of reducing the burden on the patient by decreasing the number of openings made in the abdominal wall. The medical treatment endoscope disclosed in U.S. Patent Application Publication No. 2007/0167680 may be cited as an example of a medical treatment endoscope employed in this type of procedure. This medical treatment endoscope has a flexible, soft inserted portion, and a pair of arms which are provided to the distal end of the inserted portion and have bending portions for performing bending actions. In addition, a plurality of channels are provided running through the inserted portion. A member is provided to the operating portion of the medical treatment endoscope for performing forward, backward, left and right bending manipulation of the arms. The user inserts the inserted portion of an instrument into the channel, attaches the operating portion of the instrument to the operating portion of the medical treatment endoscope, projects the distal end of the instrument out from the arm, and manipulates the operating portion to the front, back, left or right. As a result, the distal end of the instrument can be made to approach the target tissue from different directions in order to carry out the procedure.

Further, as a procedure which develops from the above-described procedure, a procedure has been proposed which is, first, inserting an endoscope into an abdominal cavity, and advancing a distal end of the endoscope into a thoracic cavity, a bladder and the like, and a treatment is performed therein. In this case, as for a body section used for approaching an abdominal cavity, an umbilical part where the scar of an incision is not going to be obvious is a suitable candidate. Thereafter, a procedure is required to incise walls of the thoracic cavity and the bladder with a treatment tool inserted into the abdominal cavity, then an endoscope is inserted into the abdominal cavity in order to pass through the perforation.

However, manipulation to pass the endoscope through the thoracic cavity and the like, is basically performed within the abdominal cavity. Therefore, it is extremely difficult to repeat inserting and retracting the endoscope through the perforation of the thoracic cavity compared with the operation through the perforation of the abdominal cavity. Furthermore, when the endoscope is advanced into the thoracic cavity by passing the endoscope through a perforation on the umbilical part, the space required for the insertion is large. In this case, it is not easy to maintain a position and direction of a distal end of a treatment tool which is used for the treatment, in particular when a flexible endoscope is used.

SUMMARY OF THE INVENTION

The present invention was conceived in view of the above-described circumstances, and has as its objective the provision of a medical instrument introduction device and a method of introducing a medical instrument which allows easy manipulation inside of, for example, the thoracic cavity, the bladder and the like, easy, even when approaching from the abdominal cavity.

A first embodiment of the present invention is a medical instrument introduction device for introducing a medical instrument into a living body provided with; a rigid main body provided with a lumen, a first fixing portion disposed on the main body to fix the main body on the first septate of the living body, and a second fixing portion disposed on a distal end side of the main body with respect to the first fixing portion for fixing the main body on a second septate which is different from the first septate.

BRIEF DESCRIPTION OF THE DRAWINGS

FIGS. 5A to C are views showing an inner needle as a modified example of the medical instrument introduction device.

FIG. 6 is a view showing a medical instrument introduction device according to a second embodiment of the present invention.

DETAILED DESCRIPTION OF THE INVENTION

The medical instrument introduction device and, a method of introducing a medical instrument according to the first embodiment of the present invention will now be explained with reference to FIGS. 1 through 7.

Figure 1:
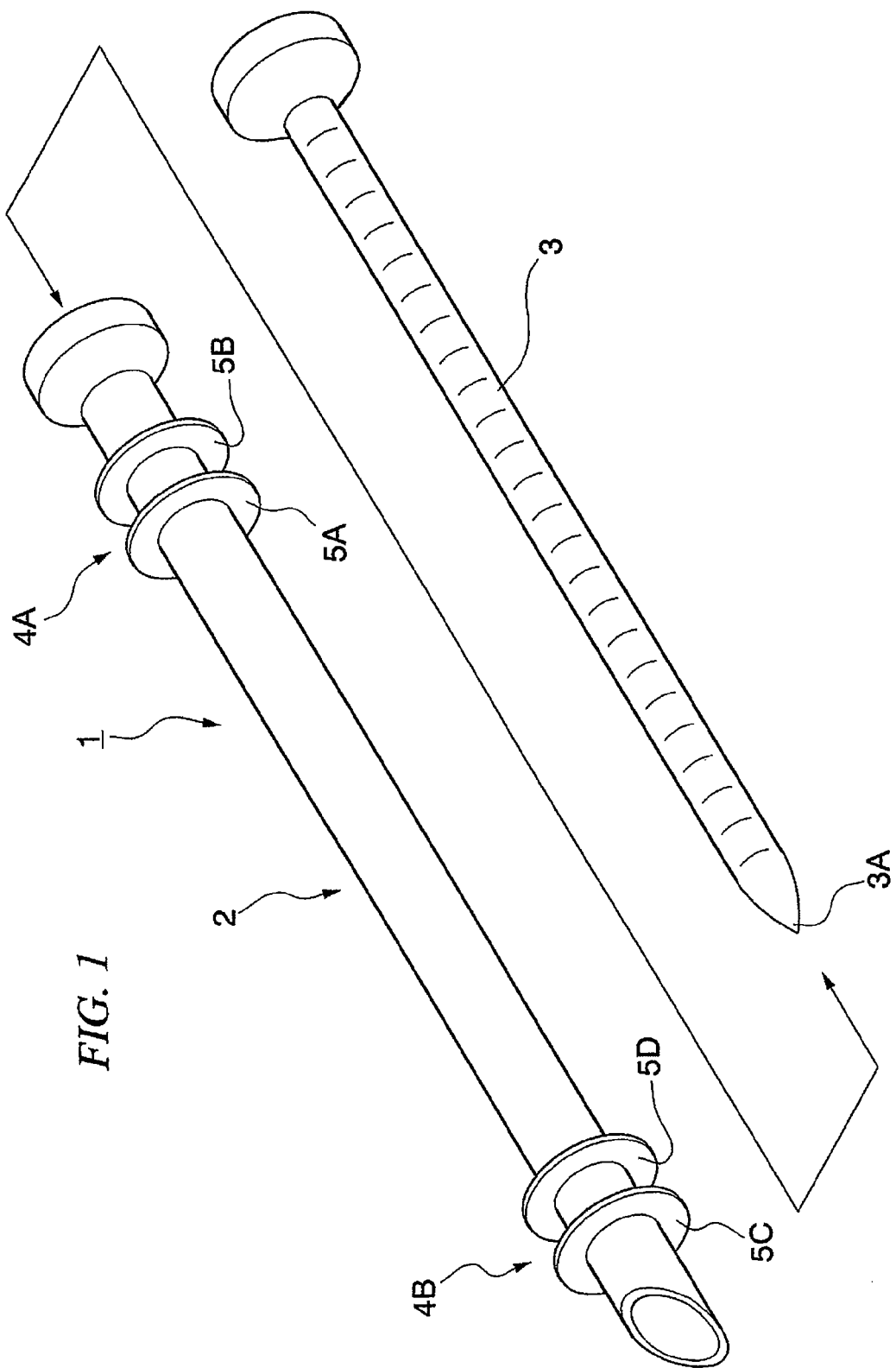
FIG. 1 is a view showing the medical instrument introduction device according to a first embodiment of the present invention.

FIG. 1 shows a medical instrument introduction device 1 (hereinafter abbreviated as 'introduction device') according to the first embodiment. This introduction device 1 is provided with a tubular main body 2, and an inner needle 3 which is inserted into the main body 2 when used.

The main body 2 is a rigid tubular member, which is not flexible. Resins, metals and the like, can be used as materials for suitably forming the main body 2 according to a user's requirement. A distal end of the main body 2 is cut slantly with respect to an axis of the main body 2 so as to be easily inserted into a through hole formed by the inner needle 3 described later.

Further, two fixing portions consisted of a pair of flanges which are substantially disc-shaped are provided on an outer peripheral surface. One of the fixing portions provided on a proximal side of the main body, the first fixing portion 4A, consists of flanges 5A and 5B which are used to fix the main body 2 with respect to an abdominal wall. On the contrary, a second fixing portion 4B consists of flanges 5C and 5D which are used to fix the main body 2 with respect to an internal dividing wall (septate) in the abdomen, such as diaphragm.

The distance between each flange at each of the fixing portions 4A and 4B is adjusted according to the thickness of, an abdominal wall and the like, to be fixed. Further, the distance between each of the fixing portions 4A and 4B are adjusted according to positions where each of the fixing portions is to be fixed. The flange 5A or 5D may be slidably disposed with respect to the main body 2 for permitting the adjustment of the distances between the flanges or between the fixing portions, and the fixing portions 4A or 4B may be constructed at any positions on the main body 2 and are held by, for example, friction, in order to improve the versatility of the introduction device.

The inner needle 3 is formed in a substantially rod-shape of metals and the like, a distal end 3A has a sharp edge so as to form a through hole inside a body. The length of the inner needle 3 is set to be slightly longer than that of the main body 2, and the diameter is set to a size which allows smooth retraction and advance movement within a lumen of the main body 2.

Figure 2:
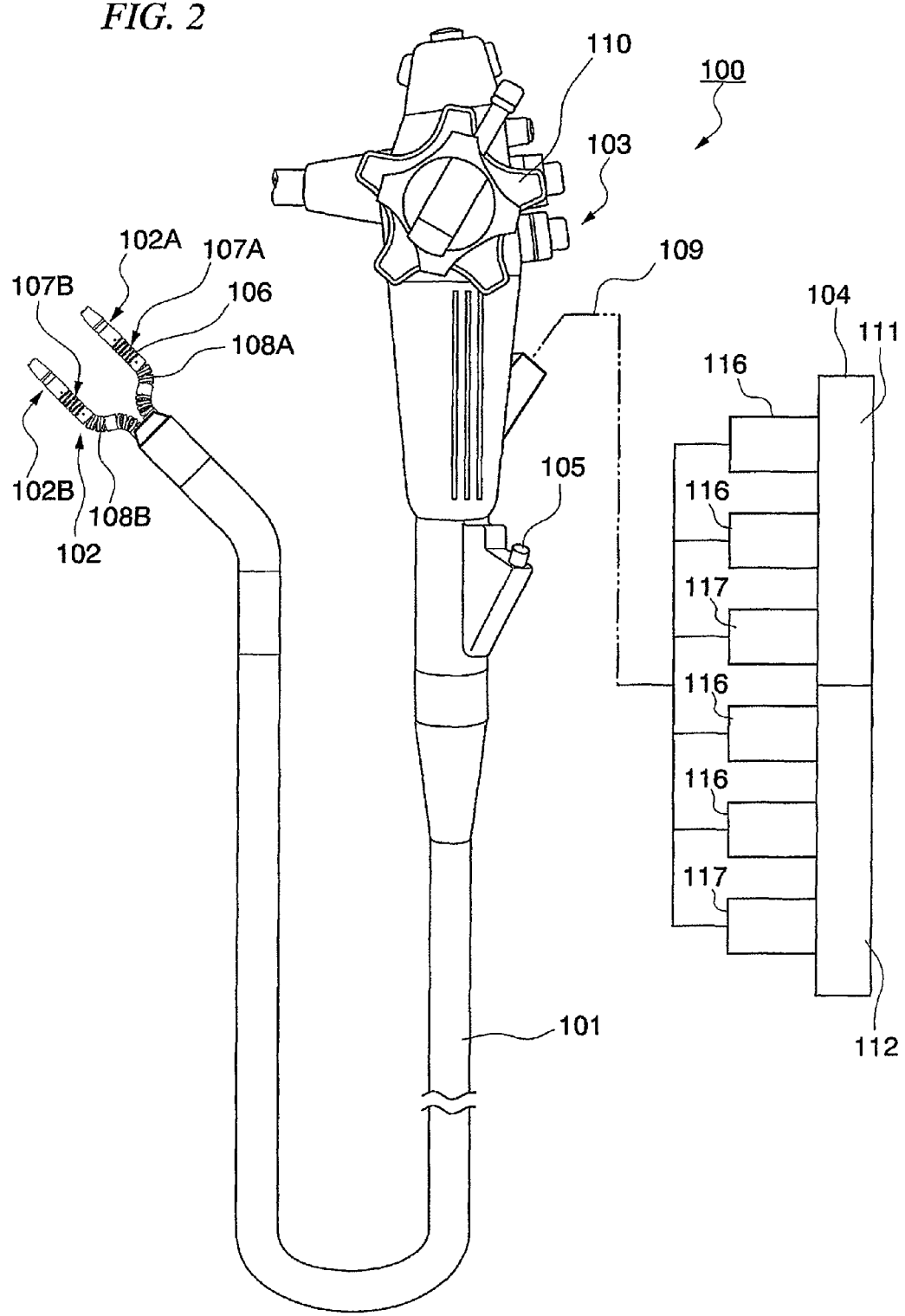
FIG. 2 is a view showing the structure of a medical treatment endoscope as an example of a medical instrument inserted into the medical instrument introduction device.

FIG. 2 shows the structure of a medical treatment endoscope 100 as an example of a medical instrument which is inserted into a body cavity using the introduction device 1. The medical treatment endoscope 100 is provided with an inserted portion 101 which is inserted into a body cavity, an arm portion 102 disposed at the distal end of the inserted portion 101, a first operating portion 103 for operating the inserted portion 101, and a second operating portion 104 for operating the arm portion 102.

The inserted portion 101 is flexible, provided with the arm portion 102 at the distal end thereof and an observation device (not shown) for observing a tissue of a body cavity. Two instrument channels which are not shown are also provided on the inserted portion 101, in which grasping forceps, a high-frequency knife, and the like, are passed therethrough. A distal end side of each of the instrument channels opens to the distal end of the inserted portion to communicate to the arm portion 102, and a proximal end side of each of the instrument channels opens to a forceps port 105 provided on the first operating portion 103.

The arm portion consists of two arms: a first arm 102A and a second arm 102B. Each of the arms 102A and 102B are tubular in shape, and communicate to the instrument channels opened to the distal end of the inserted portion 101. Therefore, a treatment tool inserted into the instrument channel can be retracted and projected from the distal end of each of the arms 102A and 102B.

Each of the arms 102A,102B are provided with first bending portions 107A,107B and second bending portions 108A, 108B consisting of a plurality of juxtaposed nodal rings 106 aligned in an axial direction. The first bending portions 107A, 107B at the distal end side can be bent to up, down, left or right with respect to the axial line of each of the arms 102A, 102B. The second bending portions 108A,108B can be bent and held in shape at a state where the distance between the distal end side of the axial lines of each of the arms 102A, 102B are spread. Both of the first and second bending portions are operated by a plurality of wires (not shown) passing through the nodal rings 106. The wires are passed through inside of the inserted portion 101 and a connecting sheath 109, and are connected to the second operating portion 104.

The first operating portion 103 has an angle knob 110 and the like, to cause a bending movement of the inserted portion 101. Further, the medical treatment endoscope 100 is connected by a universal cable (not shown) to a monitor for viewing images captured by an image capturing device disposed on the inserted portion 101, and to controlling devices and the like which perform various controlling operations. The medical treatment endoscope 100 may also be connected to known various mechanisms for insufflation, supplying a liquid, suction and the like, depending on necessity.

Figure 3:
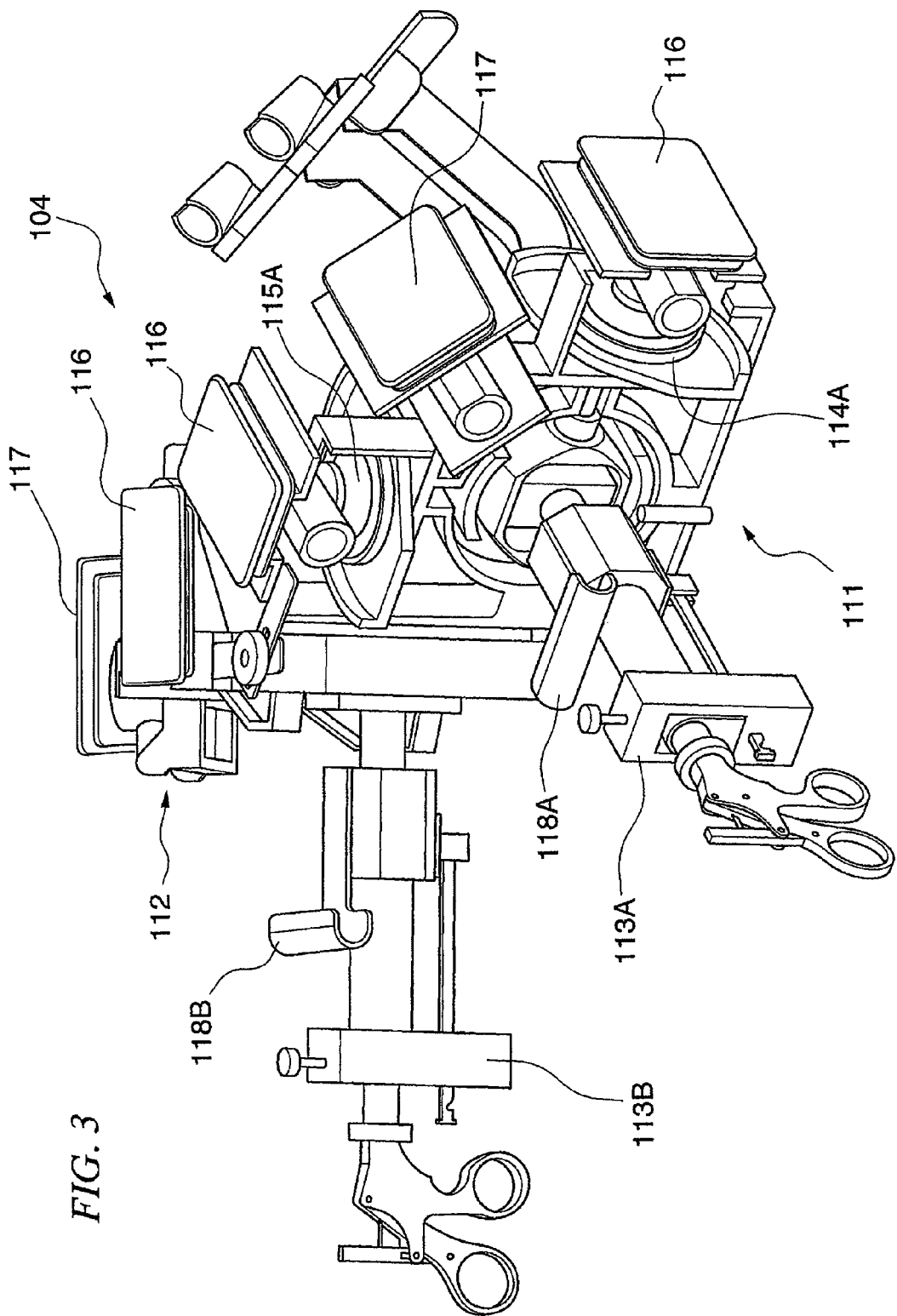
FIG. 3 is a view showing the second operating portion of the medical treatment endoscope.

FIG. 3 is a view showing an example of the second operating portion 104. The second operating portion 104 includes a first operating unit 111 for manipulating the first arm 102A and a second operating unit 112 for manipulating the second arm 102B.

Each of the operating units 111,112 are provided with operating sticks 113A,113B, respectively, which are manipulated by a user. Each of the operating sticks 113A,113B are provided with a channel inside thereof for passing a treatment tool, and each of the channels communicate with the instrument channel inside of the inserted portion 101 by being connected to the forceps port 105.

Each of the operating sticks 113A,113B are provided with first operating axes 114A,114B (not illustrated) rotating in conjunction with up and down movements of the operating sticks, and second operating axes 115A,115B (not illustrated) rotating in conjunction with left to right movements of the operating sticks. Each of the wires for operating the first bending portions 107A,107B extending by passing through the connecting sheath 109 are connected to individual first wire units 116 for each of the first bending portions 107A, 107B, and detachably disposed to the first and the second operating axes of each of the operating units 111,112.

As a result of this construction, when the operating sticks 113A,113B are inserted into a treatment tool so as to protrude from the distal end of the arm portion 102 and then manipulated up and down, left to right, a treatment mechanism disposed at the distal end of the treatment tool can be moved up, down, left or right.

Further, each of the wires for operating the second bending portions 108A,108B are connected to individual second wire units 117 for each of the second bending portions 108A,108B which are substantially the same structure as the first wire unit 116, and disposed on each of the operating units 111,112. The wires are pulled by pulling leavers 118A,118B disposed on each of the operating sticks 113A,113B toward a proximal side. As a result of this operation, the first arm 102A and the second arm 102B are bent and held in shape at a state where the distance between the axial lines of each of the arms 102A,102B is maximized.

The procedure to perform a surgical treatment by inserting the medical treatment endoscope 100 into a body cavity assisted by the introduction device 1, as disclosed above, will now be explained. In this embodiment, the procedure is explained with an example of inserting the medical treatment endoscope 100 into the thoracic cavity.

First, the user incises an abdominal wall (a first septate) in an umbilical part 120 of a patient P, who are, for example, under general anesthesia to incise a first through hole 121 thereinto for inserting the introduction device 1 into an abdominal cavity (a first body cavity). The size of the first through hole 121 may be adjusted depending on an outer diameter of the main body 2.

Figure 4:
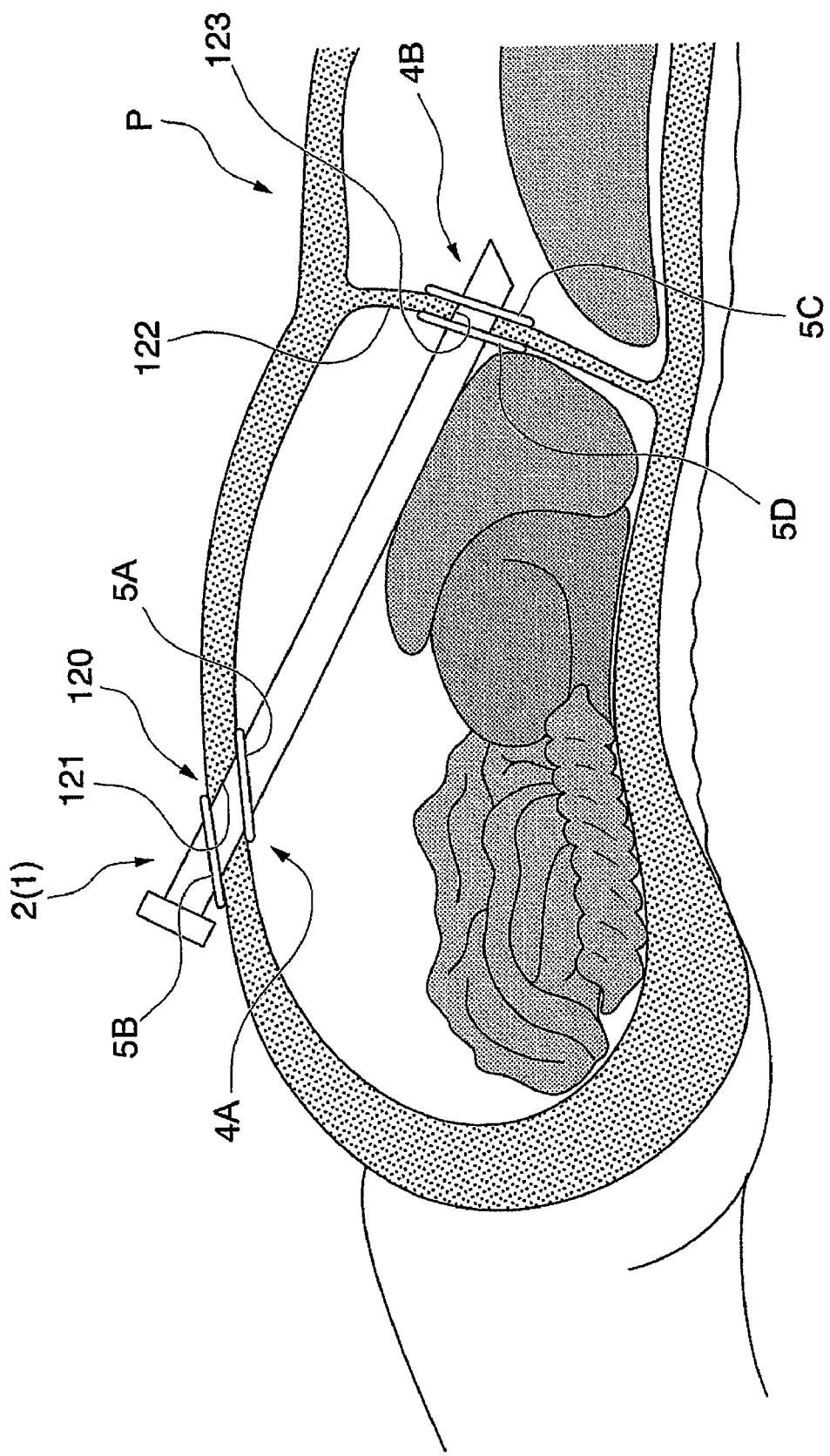
FIG. 4 is a view showing the action of the medical instrument introduction device during use.

Next, as shown in FIG. 4, the user inserts the main body 2 into the abdominal cavity from the first through hole 121 and advances the distal end of the main body 2 toward a diaphragm (a second septate) 122. At this stage, the user inserts the medical treatment endoscope 100 into the main body so as to observe a front view of the main body 2, and an incising position on the diaphragm 122 for the second through hole which communicates with the thoracic cavity (a second body cavity) is determined.

The observation for determination of the incising position may be performed by inserting a conventional endoscope into the main body 2, or may be performed with an observation device such as a laparoscope inserted via another incised position.

Next, the main body 2 is held by the user in a state where the distal end of the main body 2 abutted onto the incising position, then the inner needle 3 is inserted into the main body 2 after extracting the endoscope and the like, and inserted for observation. With the inner needle 3 abutted the diaphragm 122, a rotating operation of the inner needle 3 penetrates the diaphragm 122. As a result, the second through hole 123 is incised on the diaphragm 122.

After forming of the second through hole 123 is completed, the main body 2 is passed through the second through hole 123, the diaphragm 122 is held with the flanges 5C and 5D at the second fixing portion 4B by interposition therebetween so as to fix a position of the main body 2 with respect to the diaphragm 122. Thereafter, the position of the main body 2 is also fixed with respect to the abdominal wall by holding the abdominal wall in a vicinity of the umbilical part 120 with the flanges 5A and 5B at the first fixing portion 4A by interposition therebetween.

Note that the fixing step of the main body 2 with respect to the abdominal wall by the first fixing portion 4A may be performed prior to fixing the second fixing portion 4B or prior to the incision of the second through hole 123.

In addition, it is also preferable to provide an airtight valve and the like if the introduction device 1 is inserted into the abdominal cavity. In this case, air leakage from the thoracic cavity is prevented from achieving prevention of pneumothorax of the patient.

With the introduction device 1 fixed at two positions: at the abdominal cavity and at the diaphragm, the user inserts the medical treatment endoscope 100 into the main body 2 and projects the inserted portion 101 and the arm portion 102 from the distal end of the main body 2 into the thoracic cavity. A treatment tool employed in the operating sticks 113A, 113B of the second operating portion 104 is then inserted into the main body 2 so as to project from the distal end of the main body 2.

The user pulls leavers 118A, 118B towards the proximal side so as to hold the shape of the second bending portions 108A and 108B of the arm 102A and 102 B, respectively, in a bent state, enabling the treatment tool for ease of manipulation. Thereafter, the distal end of the treatment tool is moved up, down or left to right by manipulating the operating sticks 113A,113B via the arm portion 102, so that various treatments are performed.

After completion of the treatment inside of the thoracic cavity, the user retracts the medical treatment endoscope 100 and withdraws the main body 2 from the diaphragm 122. A treatment tool inserted into the medical treatment endoscope 100 is changed to, for example, a needle holder or the like, depending on the requirement, then the medical treatment endoscope 100 is again projected from the distal end of the main body 2 to suture the second through hole 123. After completion of suturing, the user extracts the medical treatment endoscope 100 and the main body 2 from the first through hole 121 and sutures the first through hole 121; and the entire treatment procedure is completed.

According to the introduction device 1 of the present embodiment, a passage for introducing a medical treatment device such as an endoscope is ensured to reach the thoracic cavity via the abdominal cavity assisted by the main body 2 fixed at the abdominal wall and at the diaphragm by the first fixing portion 4A and the second fixing portion 4B, respectively. Accordingly, it is possible to deliver the medical treatment endoscope 100 or the like and to recover the incised tissues or the like without contacting the organs inside of the abdominal cavity. As a result, a treatment can be performed inside of the thoracic cavity as the second body cavity without contaminating the abdominal cavity as the first body cavity.

Furthermore, since the main body 2 is formed of a rigid material, a stable passage shape is ensured. Thereby a treatment can be performed reliably with a stable manipulation since a direction and the position of a distal end of an inserted tool can be held in a stable manner, even by inserting a tool in which the inserted portion is flexible, such as the medical treatment endoscope 100.

Furthermore, since the flanges 5A and 5D are disposed at each of the fixing portions 4A and 4B, respectively, a treatment can be performed under improved clean conditions by preventing a bodily fluid or air movement between the outside of the body and the abdominal cavity, and between the abdominal cavity and the thoracic cavity.

In addition, the treatment according to the present embodiment provides the benefits of lessening the burden placed on the patient and not leaving an obvious scar after the operation, because the treatment can be performed only by perforating the first through hole 121 on the umbilical part 120.

The preceding embodiment described examples in which the distal end of the inner needle 3 is formed in a needle-shape. However, the present invention is not limited thereto; blades may be disposed parallel to an axial line of the inner needle 3 such as a blade 6, or may be spirally disposed around the inner needle 3 such as a blade 7, shown in modified examples of FIGS. 5A and 5B, respectively. Alternatively, as shown in an modified example of FIG. 5C, the inner needle 3 may be provided with an electrode 8 at the distal end thereof and a remaining portion of the inner needle 3 may be formed of an insulation material, so as to incise a through hole onto the diaphragm or the like by a high-frequency current. In this case, either monopolar or bipolar currents may be employed as a conducting method. Furthermore, distal end shapes of various conventional trocars may also be favorably employed.

Next, the second embodiment of the present invention will be explained with reference to FIGS. 6 and 7. The introduction device of the second embodiment differs from the above-described introduction device 1 with respect to the structure of the fixing portion.

Note that the compositional elements that are the same as that of the above-described introduction device 1 will be assigned the same numeric symbol, and a repetitive explanation thereof will be omitted.

FIG. 6 is a view showing an introduction device 11 in this embodiment. In this introduction device 11, a balloon 12 is disposed on the main body 2 instead of the first and second fixing portions 4A,4B. The balloon 12 is communicates with a fluid feeder (not shown) designed to be capable of inflation and deflation by feeding and collecting a fluid such as air and a saline solution thereinto. Note that other members which are capable of inflation and deflation may be disposed instead of the balloon 12.

Figure 7:
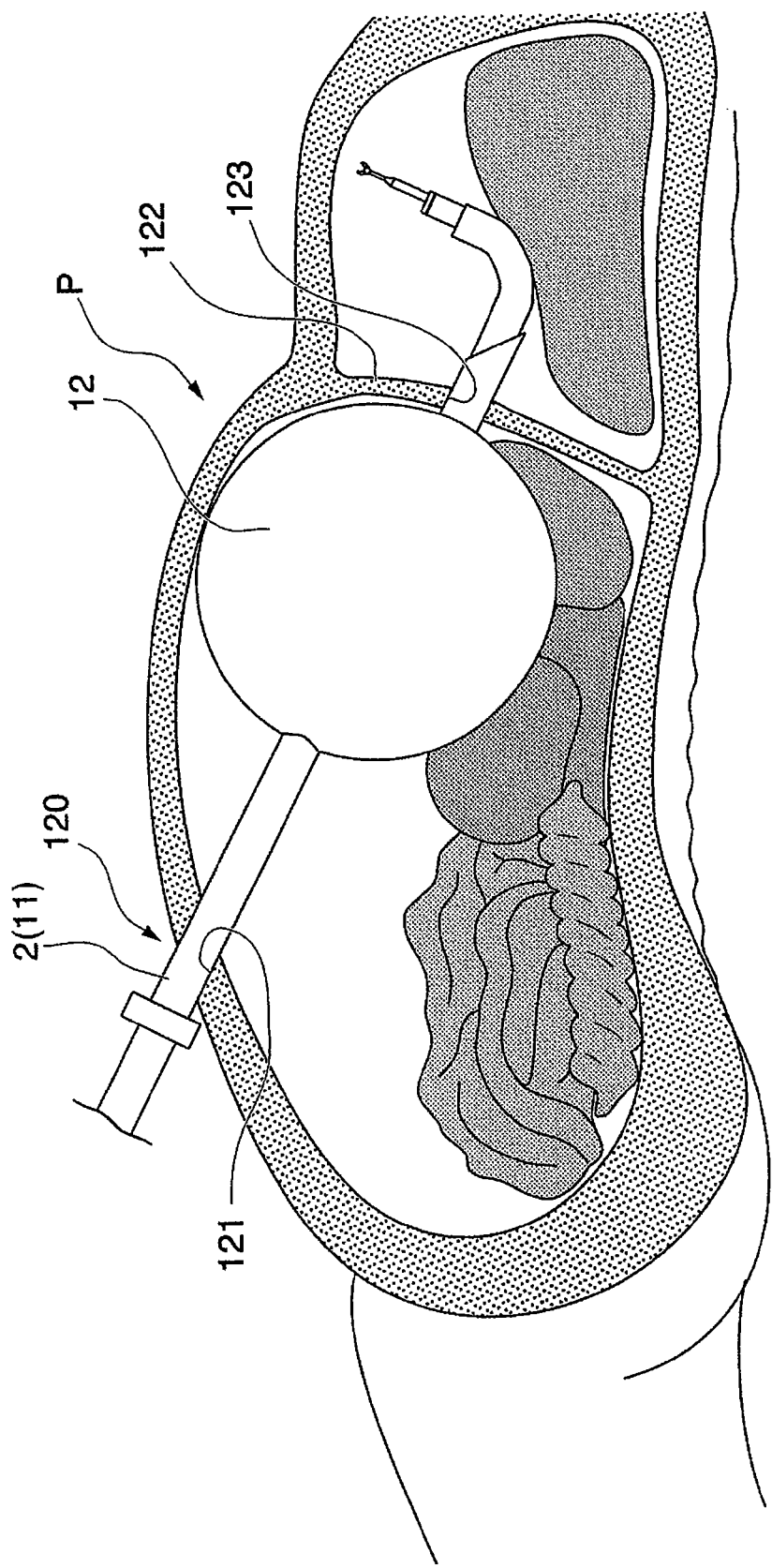
FIG. 7 is a view showing the action of the medical instrument introduction device during use.

FIG. 7 shows a state in which the introduction device 11 is being inserted into the thoracic cavity. When the introduction device 11 is inserted into the body cavity, a second through hole 123 is formed onto the diaphragm 122 with the same action of the introduction device 1 described above, and the distal end of the main body 2 is inserted into the second through hole 123. Thereafter, the user operates the fluid feeder so that a fluid is fed into the balloon 12, inflating the balloon. As a result, the main body 2 is held inside of the body cavity of a patient P. Since the size of the balloon 12 is suitably designed allowing for holding the main body 2 inside of the body cavity, the balloon 12 functions as the first and second fixing portions.

Accordingly, with the introduction device 11, it is possible to obtain the same effect obtained by the introduction device 1 as described above.

As a result of this design, since the main body 2 can be stably held inside of the body cavity by inflating the balloon 12, fixing the main body 2 can be performed with a simpler operation, compared to the clamping of a septate, such as the diaphragm, by the flanges described in the introduction device 1.

Further, an angle of the main body 2 with respect to the diaphragm 122 can be adjusted within a fixed range by adjusting the amount of a fluid fed into the balloon 12. Therefore, with a fine adjustment of the held position of the main body 2, it is possible to perform an operation by holding the main body 2 at the best position suitable for the operation.

In addition, upon withdrawal of the main body 2 from the body cavity of the patient P, the main body 2 is easily extracted by completely deflating the balloon 12 without affecting the diaphragm, the abdominal cavity and the like, achieving a lesser burden on the patient.

Next, the third embodiment of the present invention will be explained with reference to FIGS. 8 through 13. The introduction device of the third embodiment differs from the above-described introduction device 1 with respect to the structure of a main body which is flexile so as to freely bend, and the structure of the fixing portion.

Note that the compositional elements that are the same as that of the above-described introduction devices 1 and 11 will be assigned the same numeric symbol, and a repetitive explanation thereof will be omitted.

Figure 8:
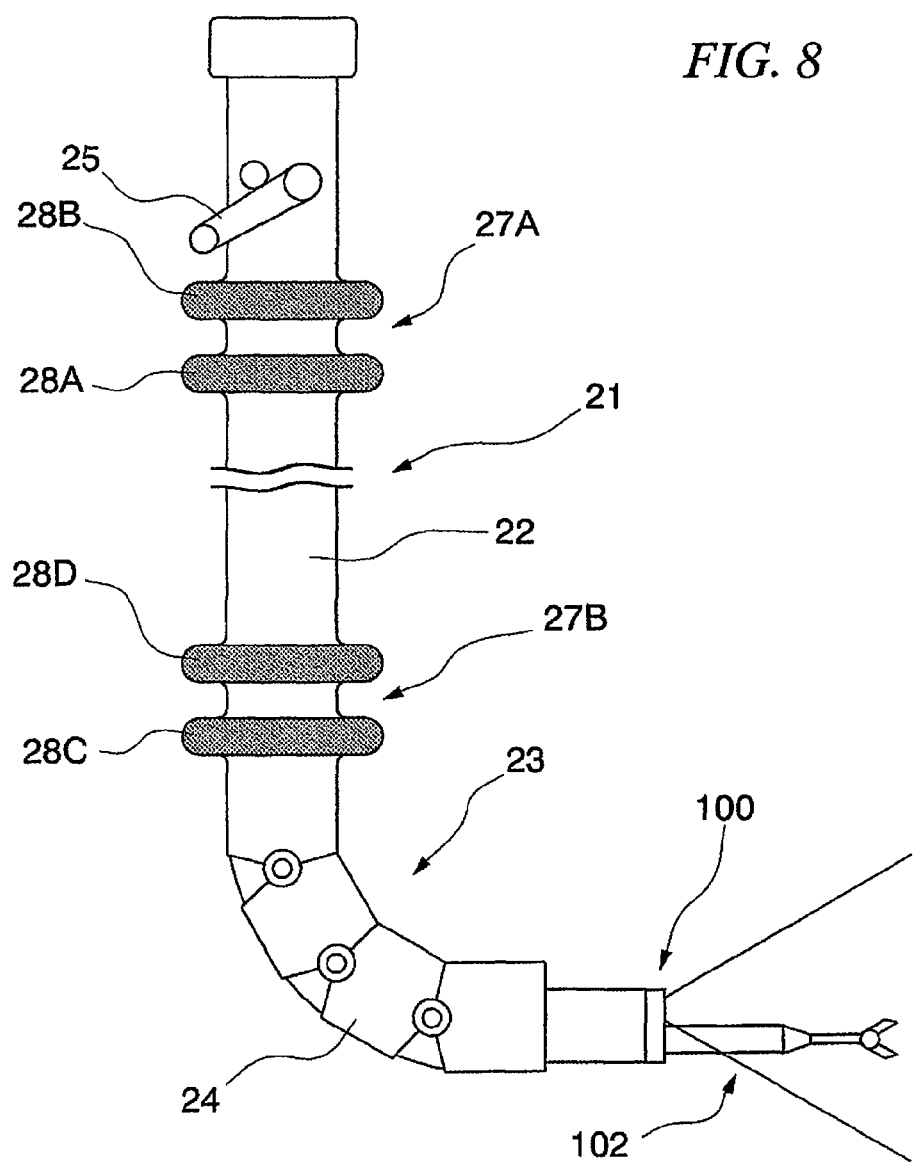
FIG. 8 is a view showing a medical instrument introduction device according to a third embodiment of the present invention.
Figure 9:
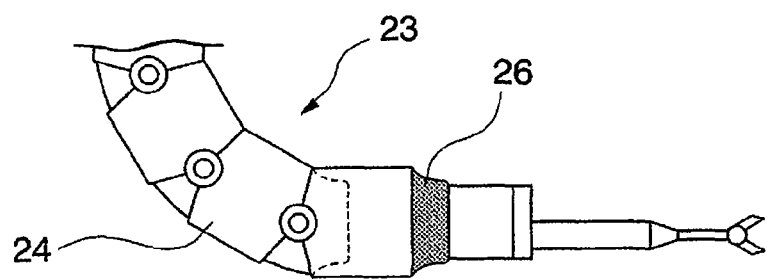
FIG. 9 is a view showing another example of the bending portion of the medical instrument introduction device.
Figure 10:
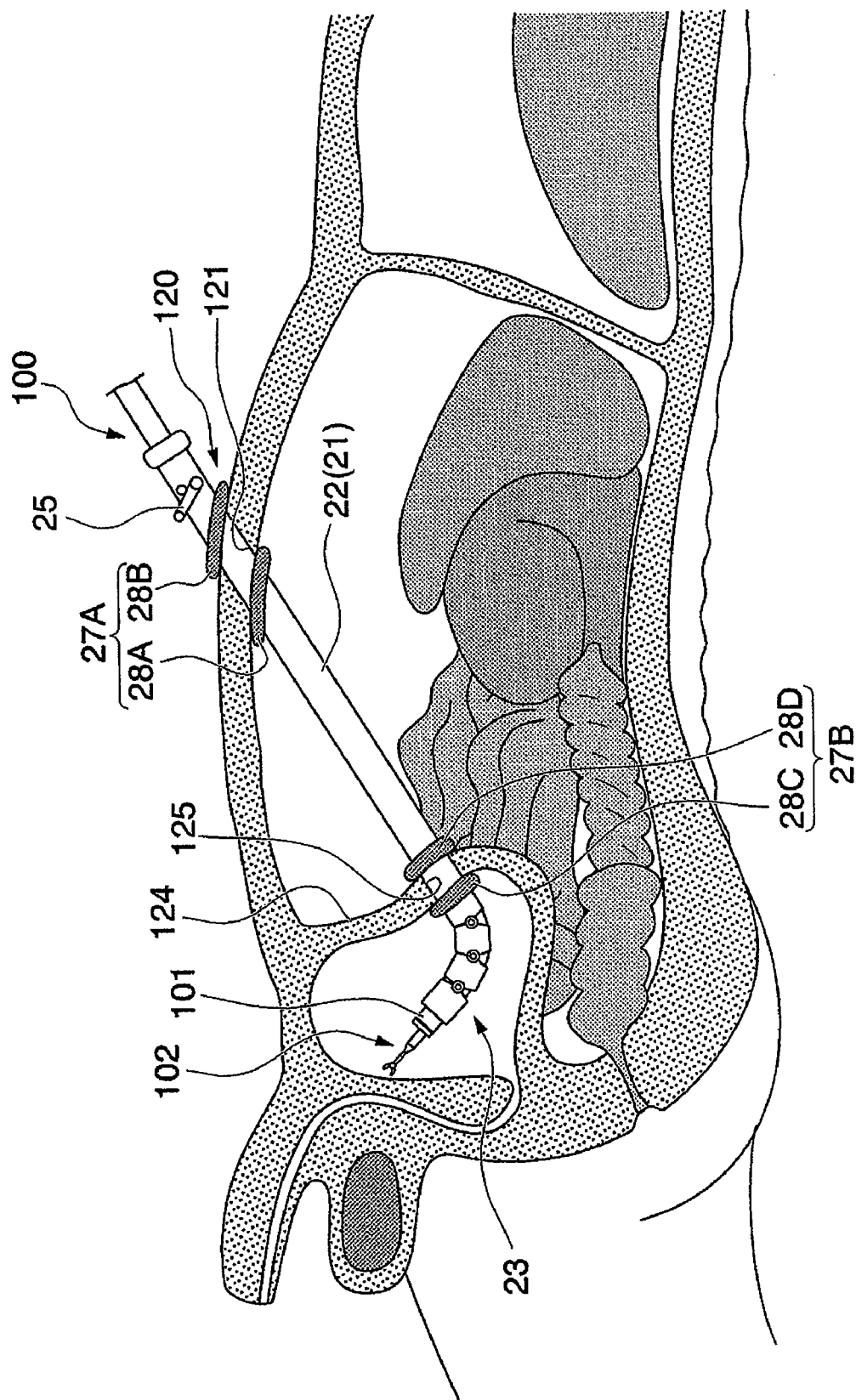
FIG. 10 is a view showing the action of the medical instrument introduction device during use.

FIG. 8 shows a state in which the medical treatment endoscope 100 is inserted into an introduction device 21 of the present embodiment. A bending portion 23 capable of bending is disposed on a distal end side of a main body 22.

A structure of the bending portion 23 is substantially the same as the first and second bending portions which are disposed on the arm portion 102 of the medical treatment endoscope 100. In particular, a plurality of juxtaposed nodal rings 24 are aligned in an axial direction, a wire not shown for operating the bending portion 23 is connected to a first nodal ring 24 from the distal end and extends to a proximal side of the main body 22 passing through each of the nodal rings 24. The wire is connected to a leaver 25 disposed on the proximal side of the main body 22. The wire is pulled by operating the leaver 25 so as to bend the bending portion 23 in a predetermined direction and to hold the bending state.

It is preferable to cover an outer surface of the nodal rings 24 with a covering member made of, for example, polyurethane or the like. By providing the covering member, an edge in the axial direction of the nodal rings 24 and the like, will not be exposed on the outer surface of the main body 22, so that effectively preventing the edges and the like from being caught onto the abdominal wall and the like can be realized. Alternatively, a valve 26 may also be provided on the nodal rings 24 of the bending portion 23 for retaining air-tightness of a passage inside of the main body 22. The valve 26 may be disposed on only an edge of the first nodal ring 24 from the distal end or may be disposed on each of the nodal rings 24.

First and second fixing portions 27A,28B of the introduction device 21 have flange-shaped paired balloons 28A,28B and 28C,28D, respectively. The balloons 28A and 28D are capable of inflation and deflation by the same mechanism employed in the balloon 12 of the above-described introduction device 11. The first fixing portion 27A is disposed on the distal end side with respect to the leaver 25, and the second fixing portion 27B is disposed on the proximal end side with respect to the bending portion 23. Alternatively, instead of the balloons 28A and 28D, other members capable of inflation and deflation may be employed as the fixing portion.

The action of the above-described introduction device 21 during use will now be explained with an example of performance of a treatment inside of a bladder by introducing the medical treatment endoscope 100 into the bladder using the introduction device 21.

First, a user creates a first through hole 121 on the umbilical part 120 with the same procedure described in the first embodiment, and then the main body 22 of the introduction device 21 is inserted into the abdominal cavity. Next, the distal end of the main body 22 is moved in the vicinity of the bladder 124, and the position where a second through hole is formed is determined while observing the bladder 124 is manipulated as described in the first embodiment. Then, the distal end of the main body 22 abuts the determined incising position and the inner needle 3 (not shown) is inserted into the main body 22, resulting in a formation of the second through hole 125 on the bladder 124.

After incising the second through hole 125, the user inserts the main body 22 into the bladder 124. Because of the provision of the bending portion 23 on the main body 22, the insertion into the bladder 124 may not be easy. In this case, with the inner needle 3 housed therein, the main body 22 may be inserted into the bladder 124 as the inner needle 3 functioning a guide. Alternatively, after extracting the inner needle 3 from the main body 22, the main body 22 may be inserted into the bladder 124 with the bending portion 23 being kept in a bent state by manipulation of the leaver 25.

When the main body 22 is inserted into the bladder 124, the user feeds a fluid into the flange-shaped balloons 28A or 28D so as to inflate. As a result, the abdominal wall and a wall of the bladder 124 are held and fixed by the first fixing portion 27A and the second fixing portion 27B, respectively.

Thereafter, the user inserts the medical treatment endoscope 100 into the main body 22 after extracting the inner needle 3, and the distal end of the inserted portion 101 and the arm portion 102 are projected from the distal end of the main body 22. The degree of bending of the bending portion 23 is adjusted and the position is held by manipulation of the leaver 25 so as to oppose the distal end of the inserted portion 101 and the arm portion 102 to a treatment target position while observing the inside of the bladder 124. At this stage, the direction of the distal end of the main body 22 may be adjusted by the user to rotate the main body 22, if necessary.

Thereafter, the user performs a treatment at the target position by using a treatment tool passed through the arm portion 102. When the main body 22 is extracted after completion of the treatment, the balloons 28A,28D at the fixing portions 27A,27B, respectively, are deflated so as to allow the extracting.

Note that the above-described treatment may be performed by the user himself/herself, or by the user accompanied by one or more assistant.

For a medical instrument such as the medical treatment endoscope 100 provided with the arm portion 103 in which the diameter is generally large, it is difficult to introduce the medical instrument via a normal route which is via the urethra for an endoscopic treatment of the bladder. However, employing the introduction device 21 of the present embodiment, a treatment can be easily performed even with the medical treatment endoscope in which the diameter is generally large by easily inserting it into the bladder 124.

The same aforementioned effects obtained by introduction devices 1 and 11 can also be obtained by the introduction device 21.

Furthermore, the bending portion 23 is disposed on the main body 22 of the introduction device 21 which is capable of retaining a desirable bending angle. As a result, a projected direction of the medical treatment endoscope 100 and the like inside of the second body cavity such as the bladder 124 and the like, can be roughly adjusted. Thereby, it is possible to project a distal end of the medical instrument such as the endoscope inserted into the introduction device 21 to a more suitable direction for the manipulation. Therefore, the treatment can be performed more easily and precisely.

Furthermore, the first and the second fixing portions 27A, 27B have balloons 28A,28D, respectively, which are capable of inflation and deflation. Thus, when the main body 22 is inserted and extracted from the patient, the main body 22 can be smoothly advanced and retracted with respect to each of the through holes 121,125 by deflating the balloons 28A, or 28D. When the main body 22 is fixed, the main body 22 can be reliably fixed by inflating the balloons. As a result of this design, the introduction steps can be performed without causing an excess burden placed on the abdominal cavity, the bladder and the like.

The preceding embodiments described examples in which the bending portion is disposed on one section on the main body. However, the bending portion may be disposed on a plurality of sections on the main body as described hereinbelow.

Figure 11:
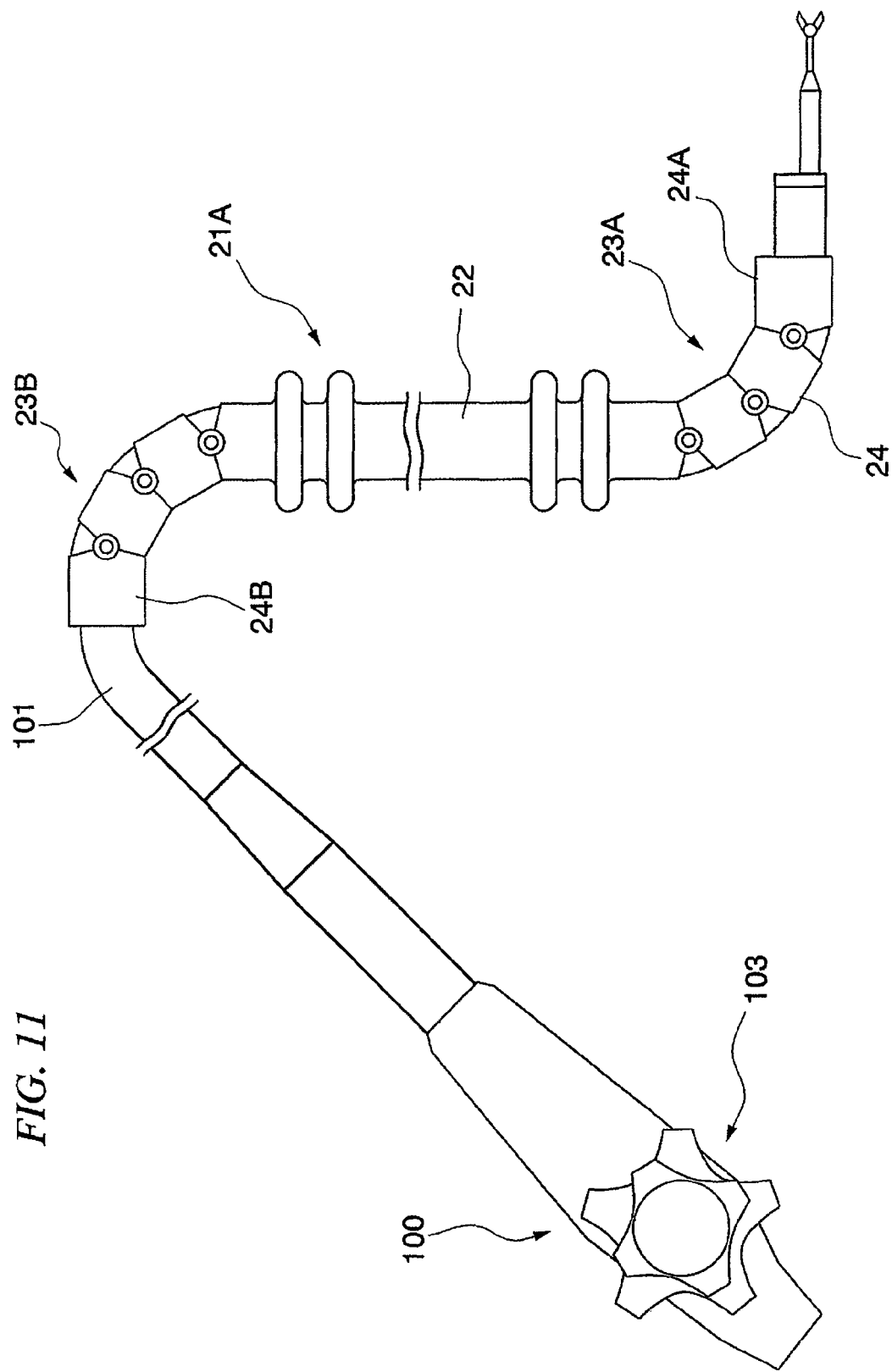
FIG. 11 is a view showing a modified example of the medical instrument introduction device according to the third embodiment.

FIG. 11 is a view of the introduction device 21A as a modified example of the proceeding embodiment. A main body 22 includes two sections of bending portions: a first bending portion 23A disposed on a distal end side and a second bending portion 23B disposed on a proximal end side. However, the leaver 25 for operating the bending portions is not provided on the introduction device 21A. Two wires (not shown) for bending each of the bending portions 23A,23B are passed through each of the nodal rings 24, such that each of the wires is opposed with respect to the axial line of the nodal rings 24. The ends of each of the wires are connected to the first nodal ring 24A from the distal end of the first bending portions 23A and the first nodal ring 24B from the proximal end of the second bending portions 23B, respectively.

As shown in FIG. 11, the medical treatment endoscope 100 is inserted into the main body 22 of the introduction device 21A designed as above, the bending portion of the inserted portion 101 is positioned at, for example, the inside of the lumen of the first bending portions 23A, and the inserted portion 101 is bent by operating the first operating portion 103, so that the first bending portion 23A is bent in conjunction with bending of the inserted portion 101. Thereafter, in conjunction with the bending of the first bending portion 23A, the wire which is fixed to the nodal rings 24 is pulled to bend the second bending portion 23B, and the main body 22 is held in a state which is bent into a substantially S-shape.

According to the aforementioned introduction device 21A described in the modified example, by operating the inserted medical treatment endoscope 100 so as to bend, the main body 22 can be bent and held in a desirable bending state without operating the leaver. Therefore, even with only one user, a treatment tool such as the endoscope can easily be inserted to adjust, for example, a direction of the distal end thereof.

While preferred embodiments of the invention have been described and illustrated above, it should be understood that these are exemplary examples of the invention and are not to be considered as limiting. Additions, omissions, substitutions, and other modifications can be made without departing from the spirit or scope of the present invention.

For example, the preceding embodiments described examples in which the medical treatment endoscope provided with the observation device and the arm portion is inserted into the introduction device. However, an inserted medical device in the present invention is not limited thereto. If a treatment can be performed with a relatively simple procedure, the treatment may be carried out by introducing a conventional endoscope which is not provided with an arm portion into the second body cavity such as the thoracic cavity or the like, using the introduction device, then the treatment may be performed with a treatment instrument inserted into an instrument channel of the endoscope.

Figure 12:
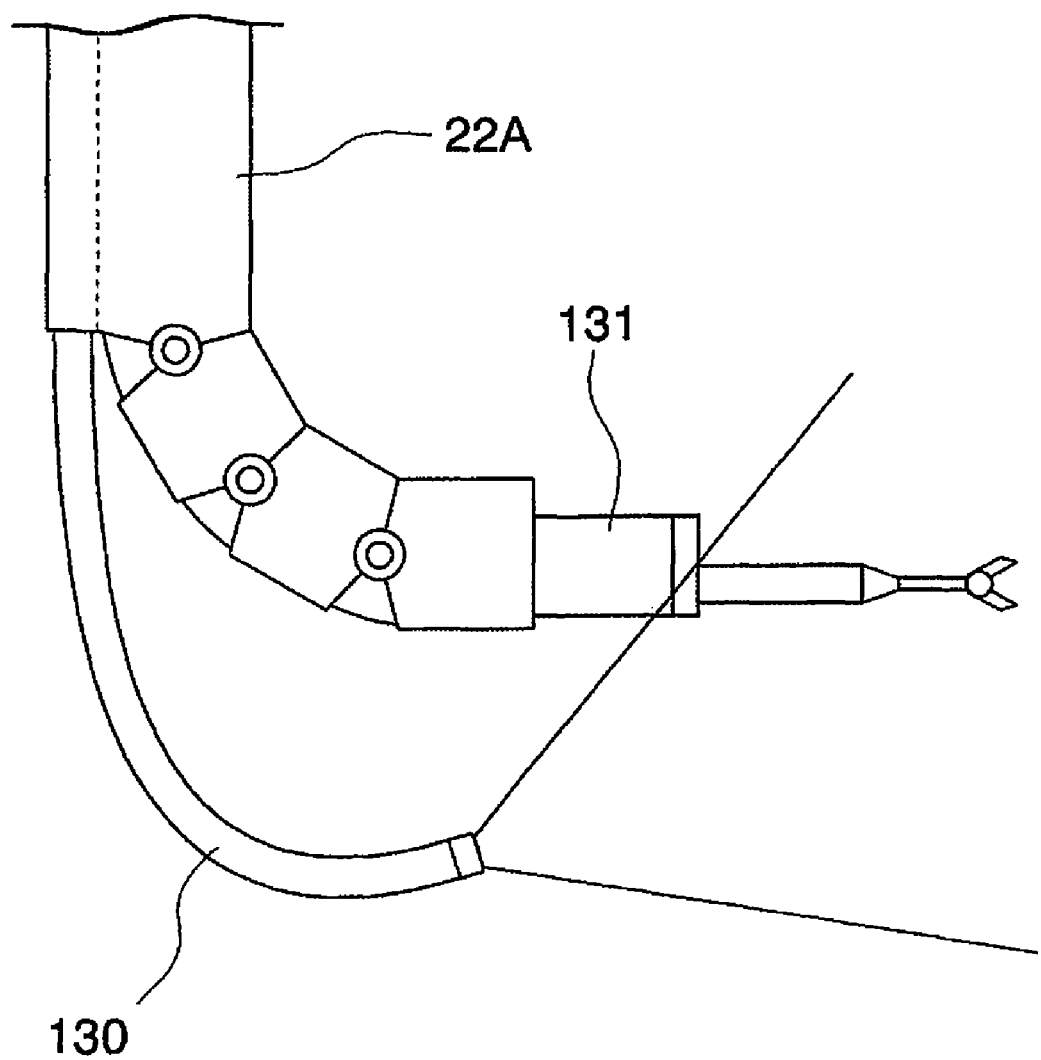
FIG. 12 is a view showing a modified example of the medical instrument introduction device according to the present invention.

As shown in a modified example of FIG. 12, it is also acceptable to provide a lumen for an endoscope and a separate lumen for a treatment tool on the main body 22A, and to project the endoscope 130 from a port which is a different port from that of the treatment tool 131, and a distal end of a treatment tool 131 and a treatment portion may be observed. Thereby, a treatment can be performed more precisely since a degree of freedom for a view point control of the endoscope 130 is improved. In this case, it is also acceptable to perform a treatment by combining the endoscope 130 and the medical treatment endoscope 100, and by employing a plurality of field of views.

Figure 13:
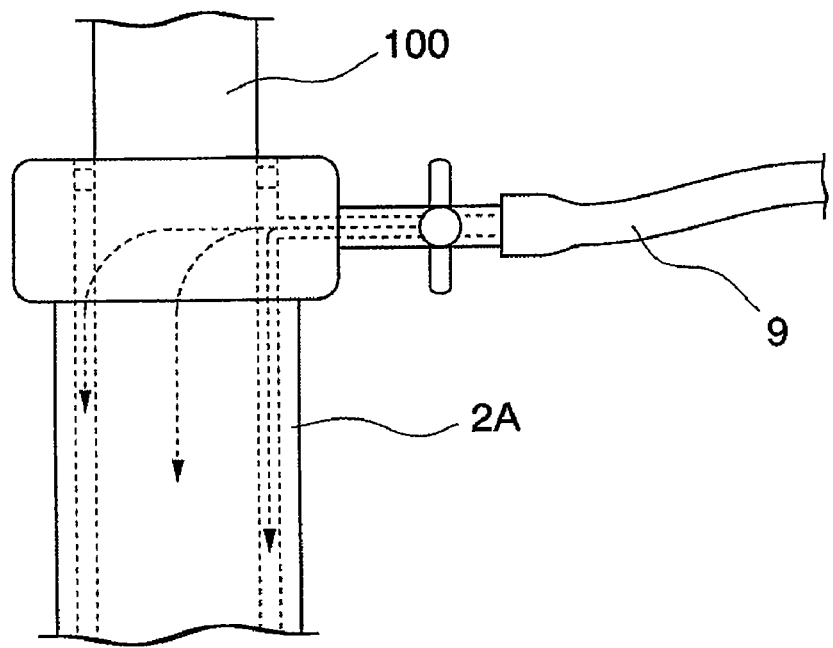
FIG. 13 is a view showing a modified example of the medical instrument introduction device according to the present invention.

Alternatively, an introduction device may be constructed by connecting a fluid feeding mechanism (not shown) to a main body 2A via the pipe 9 so as to supply a gas and a liquid via the main body 2A, as shown in a modified example of FIG. 13. In this case, the fluid may be supplied through a void created between the inserted medical treatment endoscope 100 or the like, and the lumen of the main body 2A, or a separate lumen for the fluid may also be provided. As a result of this design, a larger volume of the fluid can be supplied compared to a conventional lumen of an endoscope for insufflation and supplying a liquid. Thus, the insufflation and supplying a liquid, and suction can be suitably performed.

Figure 14:
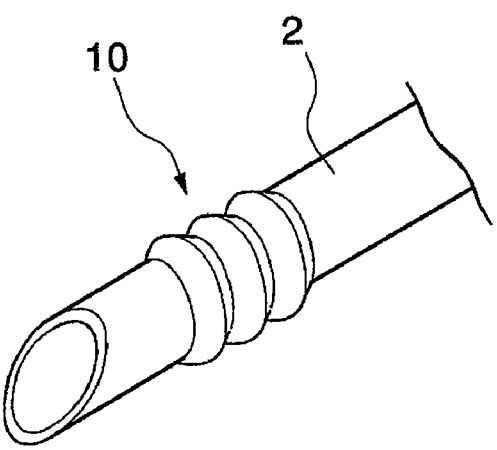
FIG. 14 is a view showing a modified example of the medical instrument introduction device according to the present invention.

Further, the preceding embodiments described examples in which the fixing portion consists of the flanges and the balloons. However, in addition to the designs, the fixing portion may also include a spiral convex portion 10, such as a thread ridge as shown in FIG. 14, or a concave portion which shapes a thread groove, or the like, disposed on the main body 2. In this case, the main body 2 can be fixed by retaining air-tightness. This is because the main body 2 is inserted into a through hole by rotating around an axial line and a tissue in the vicinity of the convex portion 10 and the like is pulled thereinto. Alternatively, by extracting the main body 2 with rotation in an opposite direction from the time of insertion, the main body 2 can be extracted without causing an excess burden on the abdominal wall and the like.

In addition, the preceding embodiments described examples of the thoracic cavity and the bladder as the second body cavity. However, the present invention is not limited thereto; other organs such as a digestive tract (i.e., a stomach, or an intestine), or a vaginal cavity, an inside of a uterus and the like, may also become a target organ as the second body cavity for the method of introducing a medical device of the present invention. Further, for a third and a forth body cavity created by further dividing the second body cavity by a septate, for example, a pericardial sac of a heart, an endoscope or the like may be introduced thereinto with a similar aforementioned method by changing the length of the introduction device, the position and the number of the fixing portions.

Finally, the invention is not to be considered as being limited by the foregoing description, and is only limited by the scope of the appended claims.

What is claimed is:

1. A medical instrument introduction device for introducing a medical instrument into a living body provided with:
    a rigid main body provided with a lumen,
    a first fixing portion disposed on the main body to fix the main body on a first septate of the living body, and
    a second fixing portion disposed on a distal end side of the main body with respect to the first fixing portion and to fix the main body on a second septate which is different from the first septate, wherein
    the first fixing portion fixes the main body on the first septate by holding the first septate from both sides of the first septate, and
    the second fixing portion fixes the main body on the second septate by holding the second septate from both sides of the second septate, the first and second fixing portions being so spaced from one another on said rigid main body as to leave a portion of said rigid main body exposed therebetween and said main body being sufficiently rigid to maintain a substantially straight shape such that the rigid main body is capable of maintaining a constant distance between the first and second septates, and
    wherein the first fixing portion and the second fixing portion are slidable with respect to the rigid main body.

2. The medical instrument introduction device according to claim 1, further comprising a bending structure portion which is capable of being bent, the bending structure portion is provided in the main body.

3. A medical instrument introduction device according to claim 1, wherein at least one of the first and the second fixing portions are designed by using a dilation material which is capable of inflating and deflating, being disposed on an outer periphery of the main body.

4. A method for introducing a medical instrument into a living body using a medical instrument introduction device according to any one of claims 1 to 3, comprising the steps of:
    forming a first through hole which is connected to a first body cavity on a surface of a living body,
    inserting a main body of the medical instrument introduction device into the first body cavity via the first through hole,
    incising a second through hole on a septate which divides the first body cavity and a second body cavity, from the first body cavity side, and connecting the first body cavity and the second body cavity,
    inserting the main body of the medical instrument introduction device into the second body cavity via the second through hole, and
    fixing the main body of the medical instrument introduction device with respect to the first through hole and the second through hole using the first fixing portion and the second fixing portion, so that the first fixing portion fixes the main body on the surface of the living body by holding the first through hole from both sides of the first through hole, and the second fixing portion fixes the main body on the septate by holding the second through hole from both sides of the second through hole.

* * * * *